United States Patent
Kobayashi

(10) Patent No.: US 9,585,689 B2
(45) Date of Patent: Mar. 7, 2017

(54) ACCESS PORT

(71) Applicant: OLYMPUS CORPORATION, Tokyo (JP)

(72) Inventor: Masayuki Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 41 days.

(21) Appl. No.: 14/549,894

(22) Filed: Nov. 21, 2014

(65) Prior Publication Data

US 2015/0080664 A1  Mar. 19, 2015

Related U.S. Application Data

(63) Continuation of application No. PCT/JP2013/064965, filed on May 23, 2013.

(30) Foreign Application Priority Data

Jun. 21, 2012 (JP) ................................. 2012-140080

(51) Int. Cl.
   *A61B 17/34* (2006.01)
   *A61B 17/02* (2006.01)
   *A61B 17/00* (2006.01)

(52) U.S. Cl.
   CPC ...... *A61B 17/3423* (2013.01); *A61B 17/0218* (2013.01); *A61B 17/3421* (2013.01);
   (Continued)

(58) Field of Classification Search
   CPC .......... A61B 17/844; A61B 2017/3425; A61B 2017/8655; A61B 2017/3435;
   (Continued)

(56) References Cited

U.S. PATENT DOCUMENTS 4,366,819 A    1/1983  Kaster
5,935,129 A *  8/1999  McDevitt ........... A61B 17/0401
                                              606/232

(Continued)

FOREIGN PATENT DOCUMENTS

JP    H09-28666 A    2/1997
JP    2010-158486 A  7/2010

OTHER PUBLICATIONS

International Search Report dated Aug. 13, 2013 issued in PCT/JP2013/064965.

(Continued)

*Primary Examiner* — David Bates
*Assistant Examiner* — Olivia C Chang
(74) *Attorney, Agent, or Firm* — Scully, Scott, Murphy & Presser, P.C.

(57) ABSTRACT

An access port is fixed to a biological membrane, such as the pericardium, in a state in which it penetrates the biological membrane. Provided is an access port including an inner tube and an outer tube fitted together so as to be movable relative to each other in an axial direction, wherein at least one of the inner tube and the outer tube has holding surfaces having substantially complementary shapes that are brought close to or away from each other by relative movement of the inner tube and the outer tube.

3 Claims, 7 Drawing Sheets

(52) U.S. Cl.
CPC  *A61B 17/3478* (2013.01); *A61B 2017/00247* (2013.01); *A61B 2017/0225* (2013.01); *A61B 2017/346* (2013.01); *A61B 2017/3425* (2013.01); *A61B 2017/3484* (2013.01); *A61B 2017/3488* (2013.01); *F04C 2270/0421* (2013.01)

(58) Field of Classification Search
CPC .... A61B 2017/0237; A61B 2017/0408; A61B 2017/348–2017/3484
See application file for complete search history.

(56) References Cited

U.S. PATENT DOCUMENTS

| | | |
|---|---|---|
| 6,007,576 A | 12/1999 | McClellan |
| 6,238,373 B1 | 5/2001 | de la Torre et al. |
| 2003/0023201 A1 | 1/2003 | Aboul-Hosn et al. |
| 2003/0093104 A1 | 5/2003 | Bonner et al. |
| 2004/0073247 A1* | 4/2004 | Loshakove ........ A61B 17/0057 606/184 |
| 2008/0086075 A1 | 4/2008 | Isik et al. |
| 2010/0081871 A1 | 4/2010 | Widenhouse et al. |
| 2012/0130193 A1 | 5/2012 | Haig et al. |

OTHER PUBLICATIONS

Extended Supplementary European Search Report dated Jan. 5, 2016 from related European Application No. 13 80 6240.1.

* cited by examiner

ACCESS PORT

CROSS-REFERENCE TO RELATED APPLICATIONS

This is a continuation of International Application PCT/JP2013/064965, with an international filing date of May 23, 2013, which is hereby incorporated by reference herein in its entirety. This application claims the benefit of Japanese Patent Application No. 2012-140080, the content of which is incorporated herein by reference.

TECHNICAL FIELD

The present invention relates to an access port.

BACKGROUND ART

A known gastric fistula catheter or trocar in the related art is equipped, at an distal end thereof, with a balloon or a superelastic expanding member that is expandable in a radial direction and that is designed to prevent the catheter or trocar from coming out by expanding the balloon or the superelastic expanding member, in a state in which it penetrates a tissue wall so that the distal end is inserted in a body (for example, see PTLs 1 and 2).

CITATION LIST

Patent Literature

{PTL 1} Japanese Unexamined Patent Application, Publication No. 2010-158486
{PTL 2} Japanese Unexamined Patent Application, Publication No. Hei 9-28666

SUMMARY OF INVENTION

The apparatuses disclosed in PTLs 1 and 2 constitute a retaining mechanism by using a member having elasticity, such as a balloon or a superelastic expanding member. Although they function effectively for a relatively thick tissue wall, they do not function as an effective retaining mechanism for a thin, highly stretchable biological membrane, such as the pericardium.

The present invention provides an access port that can be fixed to a biological membrane, such as the pericardium, in a state in which it penetrates the biological membrane.

An aspect of the present invention provides an access port comprising an inner tube and an outer tube fitted together so as to be movable relative to each other in an axial direction, wherein at least one of the inner tube and the outer tube has holding surfaces having substantially complementary shapes that are brought close to or away from each other by relative movement of the inner tube and the outer tube.

DESCRIPTION OF EMBODIMENT

Figure 1:
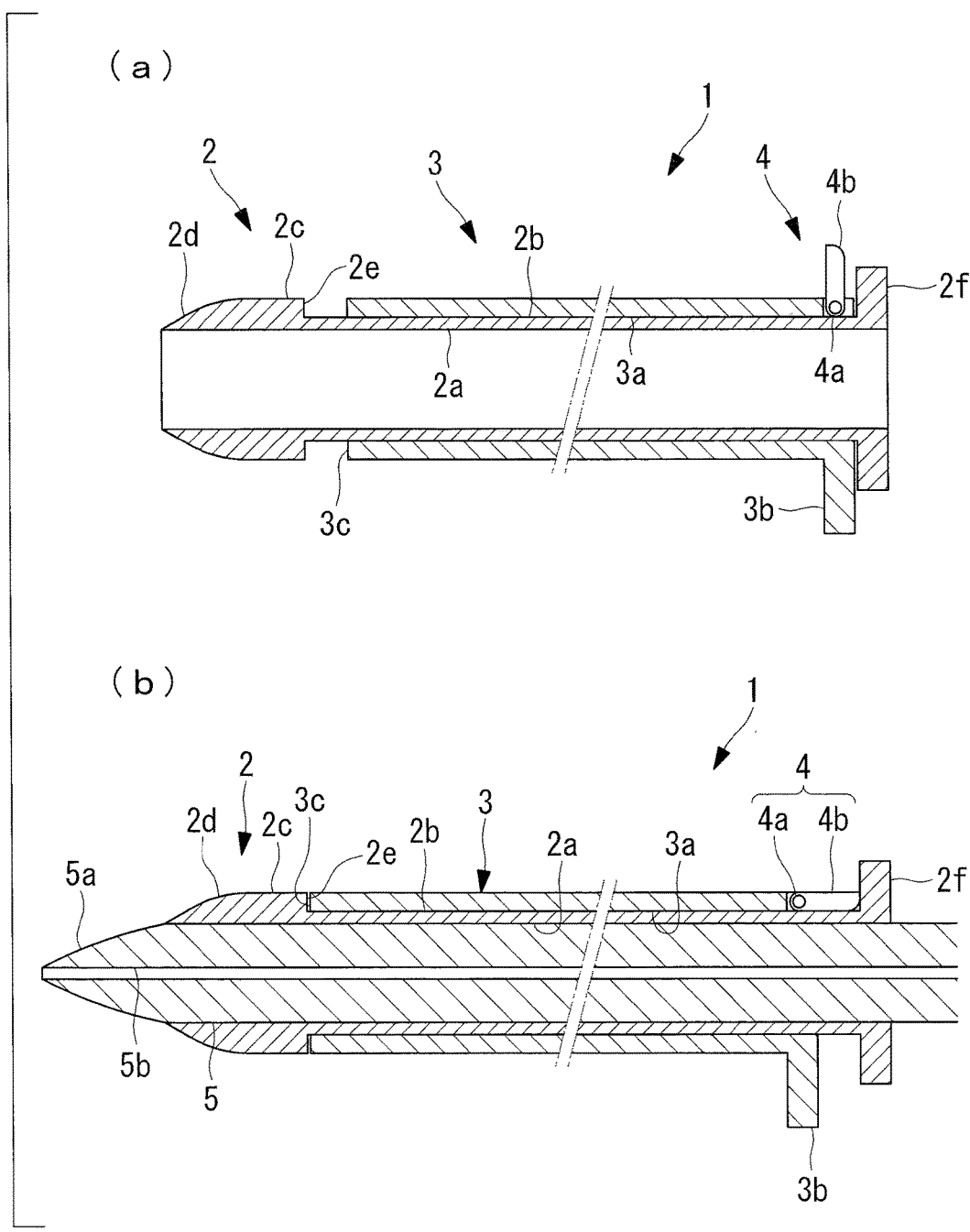
FIG. 1 is a longitudinal-sectional view of an access port according to an embodiment of the present invention, in which (a) shows an unlocked state, and (b) shows a locked state in which a dilator is inserted, respectively.

An access port 1 according to an embodiment of the present invention will be described hereinbelow with reference to the drawings.

This embodiment will be described using a pericardium A as an example of a biological membrane to which the access port 1 is to be attached.

As shown in FIG. 1(a), the access port 1 according to this embodiment is equipped with an inner tube 2 and an outer tube 3.

The inner tube 2 is provided with a through-hole 2a passing therethrough along the entire length in the longitudinal direction, a small-diameter portion 2b having a fixed outside diameter, and a large-diameter portion 2c having a larger outside diameter than that of the small-diameter portion 2b.

The large-diameter portion 2c is disposed at the distal end of the inner tube 2. A slope 2d that gradually increases in diameter from the distal end of the inner tube 2 toward the outermost diameter of the large-diameter portion 2c is provided at the distal end of the large-diameter portion 2c. Furthermore, a level-difference disposed at the boundary between the large-diameter portion 2c and the small-diameter portion 2b and having an annular flat surface 2e extending in the radial direction is provided at the rear end of the large-diameter portion 2c.

Furthermore, a flange 2f is provided at the rear end of the inner tube 2.

The outer tube 3 is shaped like a straight tube having a through-hole 3a in which the small-diameter portion 2b of the inner tube 2 is fitted so as to be movable relative thereto and is equipped with a flange 3b and a locking mechanism 4 at the rear end. The outside diameter of the outer tube 3 is arranged to be of a fixed size substantially equal to that of the large-diameter portion 2c of the inner tube 2. By fitting the small-diameter portion 2b of the inner tube 2 into the through-hole 3a of the outer tube 3, the inner tube 2 and the outer tube 3 are assembled so as to be movable relative to each other in the axial direction.

The locking mechanism 4 is equipped with a pivoting piece 4b provided so as to be pivotable about an axis 4a extending in the circumferential direction of the outer tube 3. As shown in FIG. 1(a), the lock is released in a state in which the pivoting piece 4b is placed upright in the radial direction, thus allowing the inner tube 2 and the outer tube 3 to move relative to each other. On the other hand, when the pivoting piece 4b is pivoted to a position parallel to the outer surface of the inner tube 2, as shown in FIG. 1(b), the pivot end of the pivoting piece 4b is brought into contact with the flange 2f of the inner tube 2 to fill the gap between the outer tube 3 and the flange 2f, so that the inner tube 2 and the outer tube 3 are locked to prevent relative movement in the axial direction.

As shown in FIG. 1(b), an annular flat surface 3c (a distal end face, hereinafter also referred to as a holding surface) at the distal end of the outer tube 3 and the annular flat surface 2e (an opposing surface, hereinafter also referred to as a holding surface) at the rear end of the large-diameter portion 2c of the inner tube 2 are opposed in close contact with each other or are separated by a gap smaller than the thickness of the pericardium A, with the inner tube 2 and the outer tube 3 being locked so as not to move relative to each other by the locking mechanism 4. Thus, the two flat surfaces 2e and 3c constitute holding surfaces that hold the pericardium A.

The operation of the thus-configured access port 1 according to this embodiment will be described hereinbelow.

To fix the access port 1 according to this embodiment in the state in which it penetrates the pericardium A, first, a puncture needle (not shown) is passed through the pericardium A, and a guide wire (not shown) is set in place using the puncture needle. The puncture needle is then removed so that only the guide wire remains in place, penetrating the pericardium A.

In this state, a dilator 5 is snugly fitted into the through-hole 2a of the inner tube 2 of the access port 1 according to this embodiment, as shown in FIG. 1(b). At this time, the locking mechanism 4 of the outer tube 3 is actuated to lock the inner tube 2 and the outer tube 3 so as not to move relative to each other.

The dilator 5 has, at the distal end, a tapered portion 5a that smoothly connects to the distal end of the inner tube 2 and a through-hole 5b with a diameter that allows the guide wire to be passed therethrough. With the guide wire passed through the through-hole 5b, the assembly of the dilator 5 and the access port 1 is moved forward along the guide wire. Thus, the tissue is pushed open by the tapered portion 5a at the distal end of the dilator 5, and the assembly moves forward, and furthermore, the hole formed in the pericardium A is increased in diameter by the tapered portion 5a.

Figure 2:
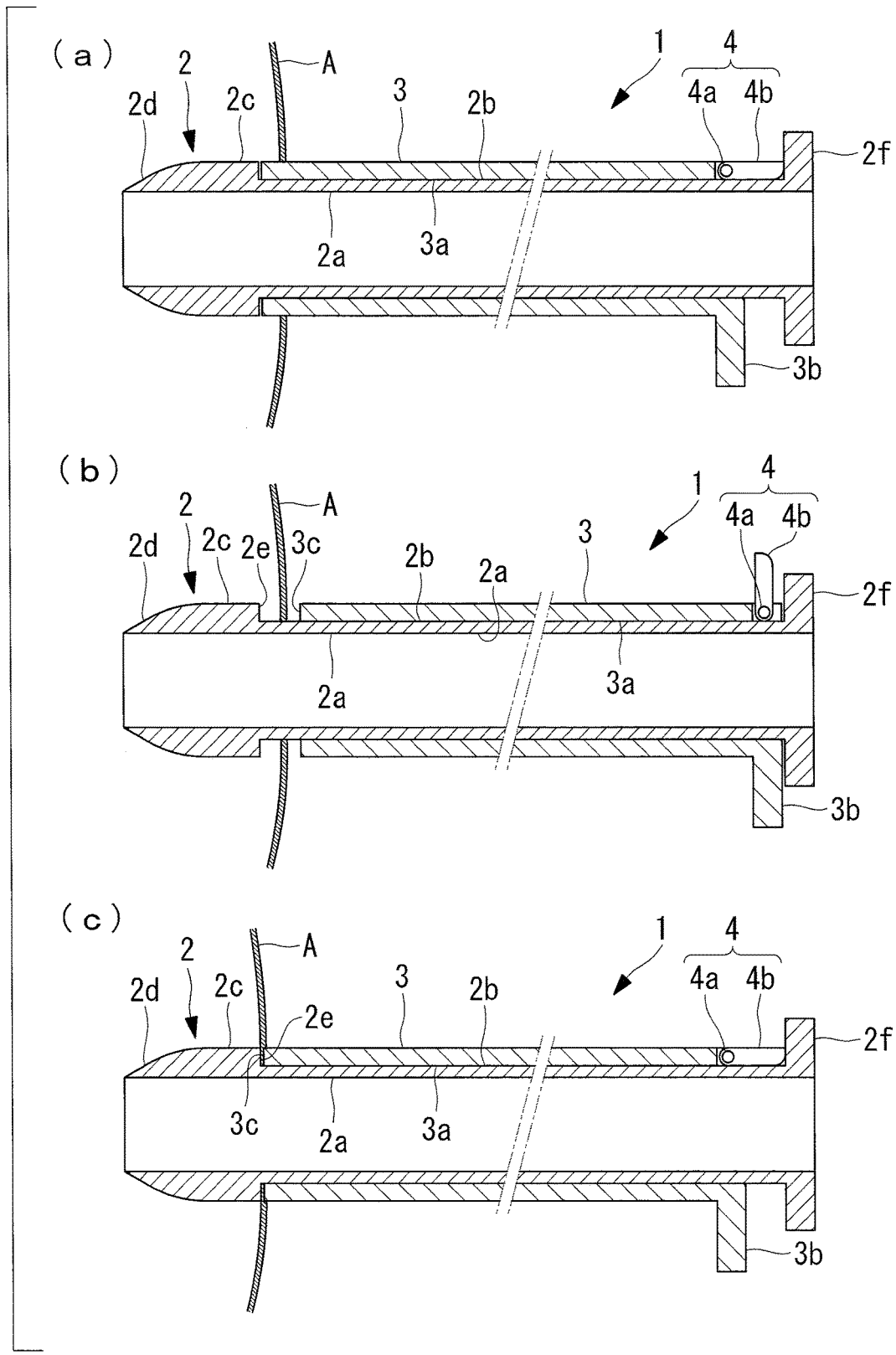
FIG. 2 is a longitudinal-sectional view of the access port in FIG. 1, in which (a) shows a state in which it is passed through the pericardium, (b) shows a state in which an outer tube is moved backwards relative to an inner tube, and (c) shows a state in which the pericardium is held between holding surfaces, respectively.

Then, once the assembly has been moved forward until the large-diameter portion 2c of the inner tube 2 completely enters the pericardium A, as shown in FIG. 2(a), the dilator 5 and the guide wire are removed.

In this state, the locking mechanism 4 is released, and the outer tube 3 is moved backwards relative to the inner tube 2, as shown in FIG. 2(b). Since this forms a gap between the large-diameter portion 2c of the inner tube 2 and the distal end face 3c of the outer tube 3, the pushed-open pericardium A causes the hole to contract due to the elasticity thereof and enters the gap.

Thereafter, as shown in FIG. 2(c), the outer tube 3 is moved forward again relative to the inner tube 2 to hold the pericardium A between the holding surfaces constituted by the distal end face 3c of the outer tube 3 and the opposing surface 2e of the large-diameter portion 2c of the inner tube 2, and the pivoting piece 4b of the locking mechanism 4 is pulled down to a position parallel to the outer surface of the inner tube 2. This causes the inner tube 2 and the outer tube 3 to be locked so as not to move relative to each other, in a state in which the peripheral portion of the hole in the pericardium A is held between the holding surfaces around the whole circumference.

Since both the distal end face 3c of the outer tube 3 and the opposing surface 2e of the inner tube 2 are parallel flat surfaces and have mutually complementary shapes, the pericardium A is held in a surface-contact manner between the holding surfaces. This allows a large frictional force to be generated between the pericardium A and the holding surfaces to keep the elastic pericardium A in the state in which it is held between the holding surfaces.

In other words, the access port 1 according to this embodiment has an advantage in that, in the state in which it penetrates the pericardium A, it can be securely fixed to the pericardium A, thus preventing it from coming out of the pericardium A.

Although this embodiment shows the flat surfaces 2e and 3c provided on the inner tube 2 and the outer tube 3 and being orthogonal to the axial direction of the inner tube 2 as an example of holding surfaces that hold the periphery of the hole in the pericardium A around the whole circumference thereof, the present invention is not limited thereto.

Figure 3:
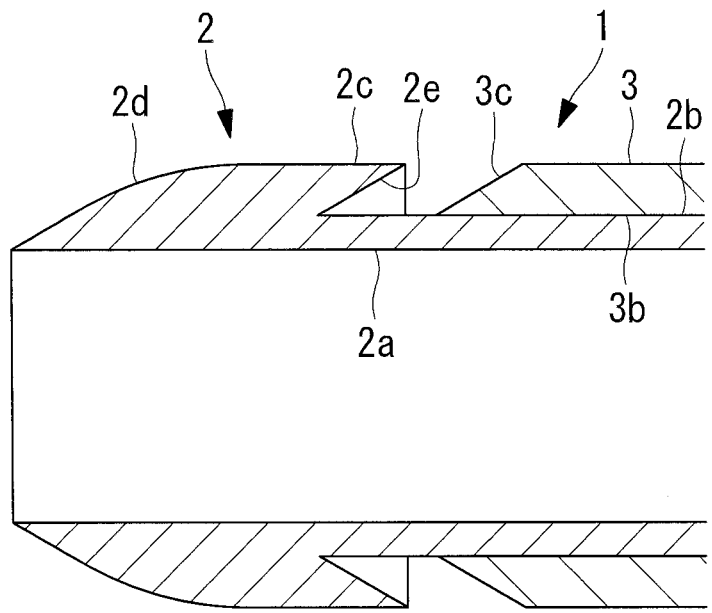
FIG. 3 is a partial enlarged longitudinal-sectional view of a first modification of the distal end of the access port in FIG. 1.

For example, as shown in FIG. 3, the distal end face 3c of the outer tube 3 may have a tapered surface shape that tapers off toward the distal end, and the opposing surface 2e of the inner tube 2 may have a tapered inner surface shape that is complementary thereto. This configuration allows the areas of the distal end face 3c and the opposing surface 2e, serving as holding surfaces that hold the pericardium A, to be increased as compared with those of the case in FIG. 1. This can increase the frictional force generated between the holding surfaces and the pericardium A, thus allowing the access port 1 to be fixed to the pericardium A more securely.

In other words, since it is preferable that the outside diameter of the access port 1 be as small as possible to be passed through tissue or the pericardium A with low invasiveness, and furthermore, that the through-hole 2a of the inner tube 2 be as large as possible to make it easy to pass a treatment tool and an endoscope therethrough, it is not possible to ensure that the radial thicknesses of the inner tube 2 and the outer tube 3 are very large. Constituting the holding surfaces from the tapered distal end face 3c and the opposing surface 2e, as described above, under such conditions allows large areas of the holding surfaces 2e and 3c for holding the pericardium A to be ensured, even if they are thin, thus allowing a larger fixing force to be generated. In other words, this has an advantage in that it is possible to provide an access port 1 that can generate a high fixing force for the pericardium A, while the outside diameter is as small as possible and the inside diameter is as large as possible.

Furthermore, by adopting the tapered holding surfaces 2e and 3c, which expand toward the rear end, as described above, when a force is exerted in a direction in which the access port 1 is withdrawn, with the pericardium A held between the holding surfaces 2e and 3c, the sharp edge at the outermost edge of the opposing surface 2e in the tapered inner surface shape can be pushed against the inner surface of the pericardium A, thus preventing the biological membrane A from being withdrawn from between the holding surfaces 2e and 3c, and thus enhancing the retaining effect.

Figure 4:
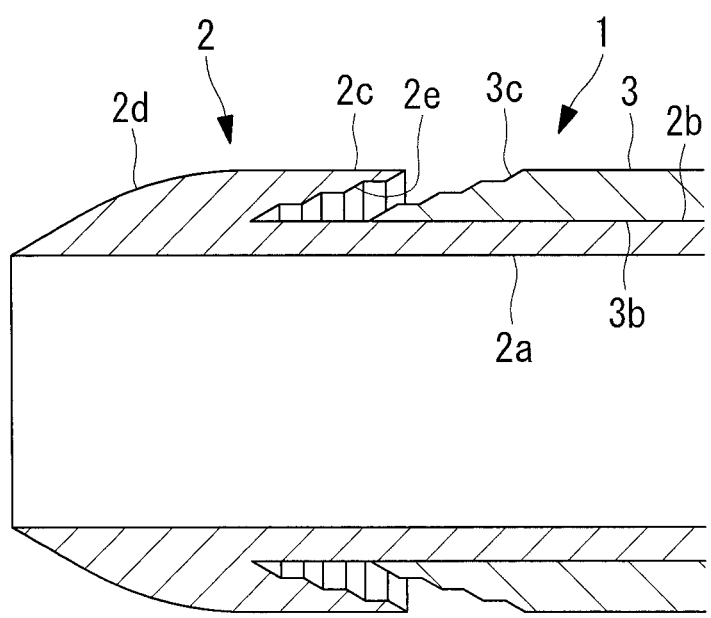
FIG. 4 is a partial enlarged longitudinal-sectional view of a second modification of the distal end of the access port in FIG. 1.
Figure 5:
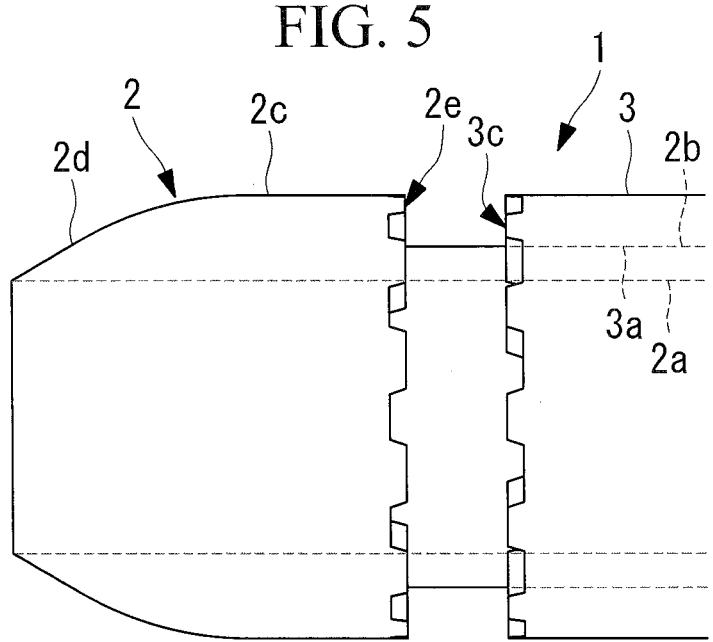
FIG. 5 is a partial enlarged longitudinal-sectional view of a third modification of the distal end of the access port in FIG. 1.

Furthermore, the holding surfaces 2e and 3c may be provided with a plurality of protrusions and indentions in the radial direction, as shown in FIG. 4, or may be provided with a plurality of protrusions and indentions in the circumferential direction, as shown in FIG. 5.

Providing the plurality of protrusions and indentions in the radial direction has the advantage that the contact area can be further increased, and even if a radial extracting force is exerted on the held pericardium A, the frictional force acting against it can be increased.

Furthermore, providing the plurality of protrusions and indentions in the circumferential direction can also further increase the contact area and can prevent the holding surfaces 2e and 3c that hold the pericardium A from rotating relative to each other in the circumferential direction, thus similarly preventing the held pericardium A from being withdrawn.

Figure 6:
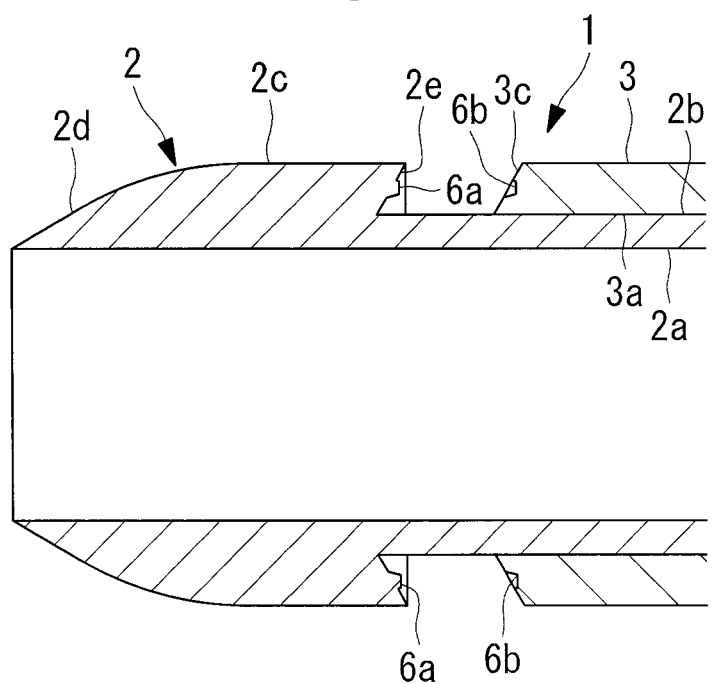
FIG. 6 is a partial enlarged longitudinal-sectional view of a fourth modification of the distal end of the access port in FIG. 1.

Furthermore, it is also possible to achieve both of the advantages in FIGS. 4 and 5 by providing a protruding portion 6a on one of the holding surfaces 2e and 3c and an indented portion 6b on the other, as shown in FIG. 6, and by engaging them with each other. Although FIG. 6 shows that the protruding portion 6a and the indented portion 6b are provided at one location in the radial direction, they may be provided at a plurality of locations. Alternatively, they may be provided at a plurality of locations at intervals in the circumferential direction.

Figure 7:
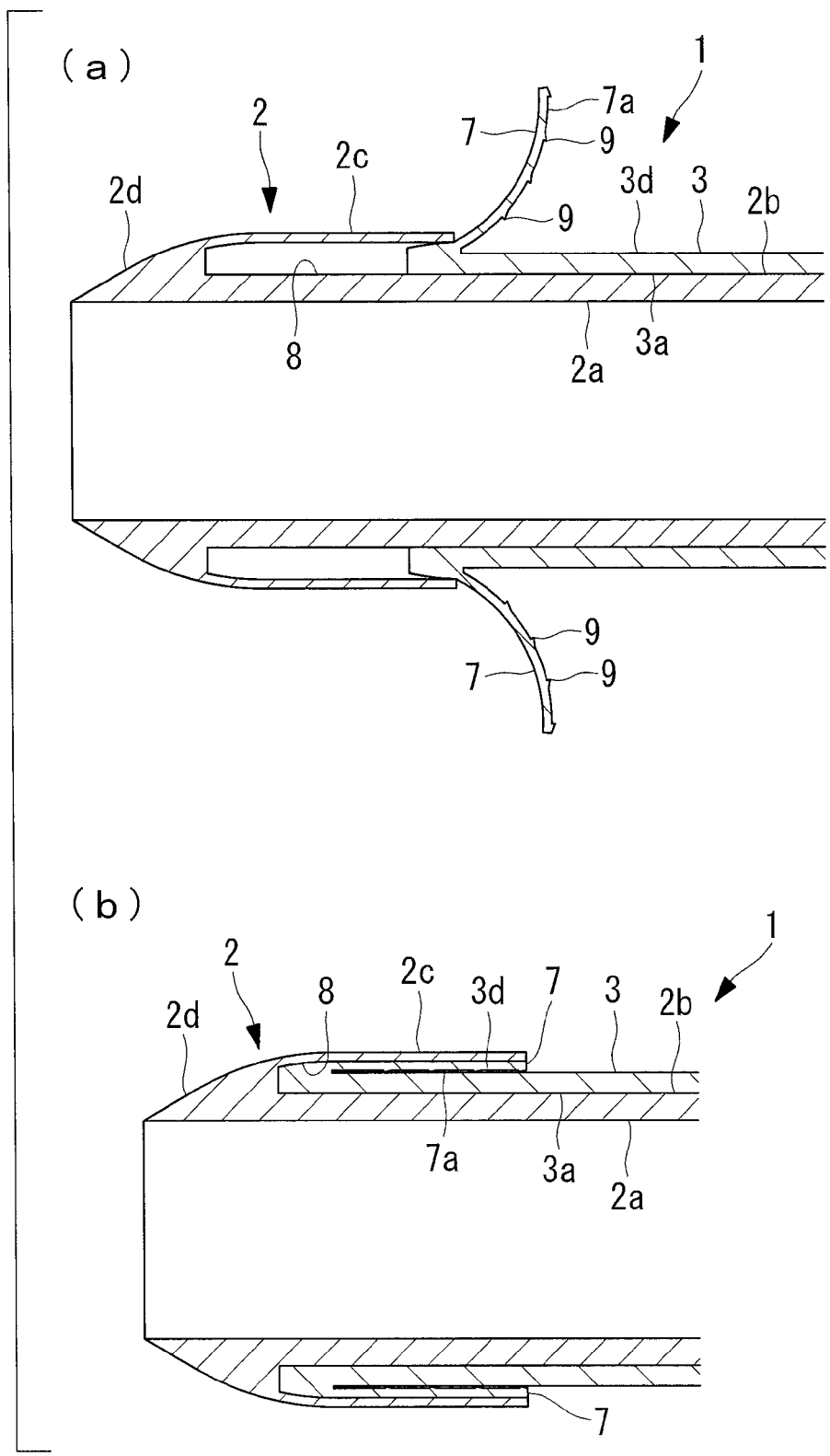
FIG. 7 is a partial enlarged longitudinal-sectional view of a fifth modification of the distal end of the access port in FIG. 1, in which (a) shows a state in which an outer tube is moved backwards relative to an inner tube, and (b) shows a state in which the outer tube is moved forwards relative to the inner tube, respectively.

Furthermore, in this embodiment, the holding surfaces that hold the pericardium A are constituted by the distal end face 3c of the outer tube 3 and the opposing surface 2e of the inner tube 2; instead, two holding surfaces may be provided at the outer tube 3, as shown in FIG. 7.

Specifically, in an example shown in FIG. 7(a), a plurality of strip-shaped pulling-in members 7 made of a flexible material, such as spring steel, one end of which is fixed to the distal end of the outer tube 3, are provided in the circumferential direction, and an accommodating portion 8 that can accommodate the pulling-in members 7 parallel to the outer surface of the outer tube 3 is provided at the inner tube 2 side, as shown in FIG. 7(b). The surfaces of the pulling-in members 7 facing the outer surface of the outer tube 3 are provided with a plurality of projections 9. Thus, the holding surfaces are constituted by surfaces 7a of the pulling-in members 7 and the outer surface 3d of the outer tube 3.

After the thus-configured access port 1 penetrates the pericardium A, with the distal end of the outer tube 3 and the pulling-in members 7 accommodated in the accommodating portion 8 of the inner tube 2, as shown in FIG. 8(a), the outer tube 3 is moved backwards relative to the inner tube 2 to extract the pulling-in members 7 from the accommodating portion 8 to allow the surfaces 7a thereof to come into close contact with the inner surface of the pericardium A, as shown in FIG. 8(b). Thereafter, the inner tube 2 is moved backwards relative to the outer tube 3, as shown in FIG. 8(c).

Thus, the pulling-in members 7 and the distal end of the outer tube 3 are pulled into the accommodating portion 8 of the inner tube 2. At that time, the pericardium A that is in close contact with the surfaces 7a of the pulling-in members 7 is pulled together therewith into the accommodating portion 8 of the inner tube 2, while being held between the holding surfaces constituted by the surfaces 7a of the pulling-in members 7 and the outer surface 3d of the outer tube 3. Since the pulling-in members 7 are provided at a plurality of locations in the circumferential direction, the pericardium A is pulled into the accommodating portion 8 in a state in which the pericardium A is held between the holding surfaces at those locations in the circumferential direction.

Figure 8:
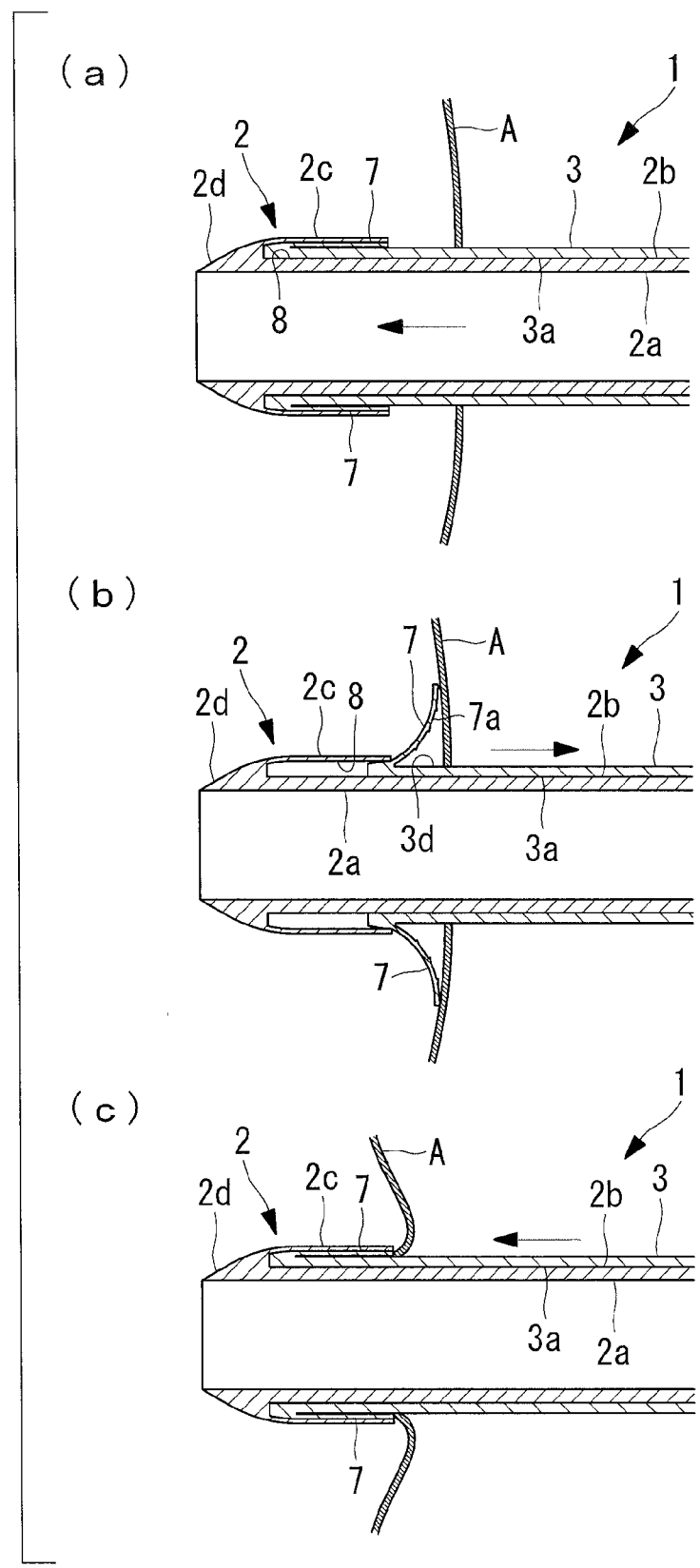
FIG. 8 is a partial enlarged longitudinal-sectional view of the access port in FIG. 7, in which (a) shows a state in which it is passed through the pericardium, (b) shows a state in which the outer tube is moved backwards relative to the inner tube, and (c) shows a state in which the inner tube is moved backwards relative to the outer tube, and the pericardium is pulled in between holding surfaces, respectively.

Thus, since the holding surfaces 3d and 7a that hold the pericardium A are disposed parallel to the axial direction of the inner tube 2, larger areas thereof can be ensured, and thus, the retaining effect can be enhanced. Another advantage is that engaging the projections 9 provided on the surfaces 7a of the pulling-in members 7 with the pericardium A can further enhance the retaining effect. Although FIGS. 7 and 8 show the plurality of strip-shaped pulling-in members 7 provided in the circumferential direction, a single strip-shaped pulling-in member may be provided at one location. Furthermore, the strip-shape is not limited to a rectangle; the strip-shaped pulling-in member 7 may have a sector shape increasing in width from the base end thereof toward the distal end or a shape in which the distal end of the pulling-in member 7 is divided into a plurality of pieces.

Figure 9:
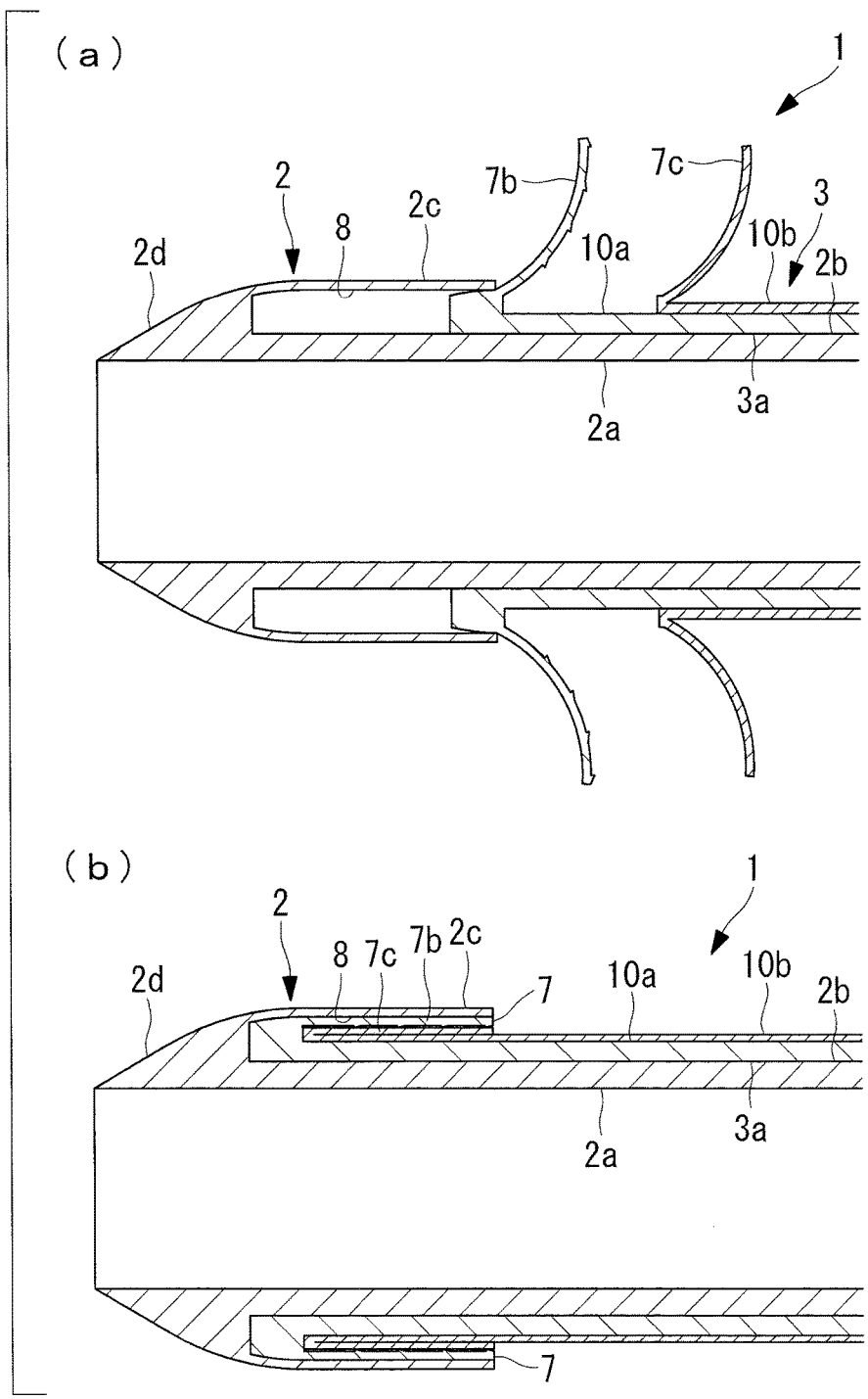
FIG. 9 is a partial enlarged longitudinal-sectional view of a sixth modification of the access port in FIG. 1, in which (a) shows a state in which pulling-in members of two outer tubular portions are separated from each other, and (b) shows a state in which the pericardium is held between pulling-in sections and accommodated in an accommodating portion, respectively.

Alternatively, as shown in FIG. 9, it is also possible to provide pairs of outer tubular portions 10a and 10b that can move relative to each other and strip-shaped pulling-in members 7b and 7c and to accommodate the pulling-in members 7b and 7c in the accommodating portion 8 of the inner tube 2, with the pericardium A held between the holding surfaces constituted by the opposing surfaces of the two pulling-in members 7b and 7c. This has an advantage that the pericardium A can be pulled into the accommodating portion 8 more reliably because the pulling-in members 7b and 7c are accommodated therein after the pericardium A is held between the holding surfaces.

Furthermore, although this embodiment shows the pericardium A as an example of a biological membrane, it is not limited thereto; the present invention may be applied to an access port 1 fixed to any other biological membrane in a state in which it penetrates the biological membrane.

Furthermore, although the locking mechanism 4 is constituted by the pivoting piece 4b, any structure may be adopted instead.

Furthermore, the holding surfaces constituted by the flat surfaces 2e and 3c extending in the radial direction, as shown in FIG. 1, may be provided with protrusions and indentions to enhance the retaining effect.

According to the above embodiment, following aspects can be introduced.

An aspect of the present invention provides an access port comprising an inner tube and an outer tube fitted together so as to be movable relative to each other in an axial direction, wherein at least one of the inner tube and the outer tube has holding surfaces having substantially complementary shapes that are brought close to or away from each other by relative movement of the inner tube and the outer tube.

According to this aspect, the holding surfaces provided on at least one of the inner tube and the outer tube are moved away from each other by moving the inner tube and the outer tube relative to each other in the axial direction, with the inner tube penetrating the biological membrane via a hole formed in the biological membrane. By disposing the biological membrane between the holding surfaces, and thereafter moving the inner tube and the outer tube relative to each other in the axial direction again to bring the holding surfaces close to each other, the biological membrane can be held in the thickness direction thereof. In this case, since the holding surfaces have substantially complementary shapes, the biological membrane can be held over a wide area in a surface-contact manner, thus allowing the access port to be securely fixed in a state in which it penetrates the biological membrane so that it does not come out. Thus, a device can easily be inserted into the biological membrane from the outside of the biological membrane via the through-hole in the inner tube.

In the above aspect, the holding surfaces may be constituted by a distal end face of the outer tube and an opposing surface provided at a position on a distal end of the inner tube opposing the distal end face.

Since this decreases the diameter of the inner tube by one step at the position of the opposing surface from the distal end to the rear end, when the inner tube is passed through the biological membrane while pushing open the hole in the biological membrane, the inside inner tube decreases in diameter at the point where the biological membrane has gone past the opposing surface, the hole in the biological membrane contracts due to the elasticity thereof to bring the biological membrane in between the distal end face of the outer tube and the opposing surface of the inner tube. Accordingly, by moving the outer tube relative to the inner tube toward the distal end of the inner tube, the biological membrane can easily be held between the holding surfaces constituted by the distal end face and the opposing surface.

Furthermore, in the above aspect, the distal end face of the outer tube may have a tapered surface shape that tapers toward the distal end; and the opposing surface of the inner tube may have a tapered inner surface shape.

This allows the biological membrane to be held between the holding surfaces constituted by the distal end face having the tapered surface shape and the opposing surface having the tapered inner surface shape. This can increase the area as compared with holding surfaces that are orthogonal in the axial direction, thus allowing the biological membrane to be held over a wider area more reliably and allowing the access port to be securely fixed to the biological membrane.

Furthermore, the portion of the biological membrane around the hole, held by the thus-formed holding surfaces, is folded back in the direction of the distal end of the inner tube as it approaches the inside in the radial direction. As a result, even if a force in a direction in which the access port is withdrawn is exerted thereon, the sharp edge at the outermost edge of the opposing surface in the tapered inner surface shape pushes against the biological membrane, preventing the biological membrane from being withdrawn from between the holding surfaces, and thus, the retaining effect can be enhanced.

In particular, since it is preferable that the access port be insertable into the body via a small hole and have a large-diameter through-hole therein, it is not possible, in many cases, to ensure that the radial thicknesses of the inner tube and the outer tube are large. Accordingly, adopting the above holding surfaces can ensure a large area of the holding surfaces while reducing the thicknesses of the inner tube and the outer tube, thereby enhancing the biological membrane retaining effect.

Furthermore, in the above aspect, the distal end face and the opposing surface may be provided with a protrusion and an indention.

This can further increase the area of the holding surfaces, and engagement of the indented portion and the protruding portion can increase the effect of keeping the biological membrane held therebetween in the held state.

Furthermore, in the above aspect, the protrusion and the indention of the distal end face and the opposing surface may be provided in a circumferential direction.

This can increase the area of the holding surfaces, and engagement of the indented portion and the protruding portion provided in the circumferential direction can prevent the inner tube and the outer tube from rotating relative to each other in the circumferential direction. This can prevent displacement from occurring between the holding surfaces and the biological membrane due to relative rotation, and can prevent the biological membrane held between the holding surfaces from being withdrawn.

Furthermore, in the above aspect, a strip-shaped pulling-in member formed of a flexible material, one end of which is attached to the distal end of the outer tube, may be provided; and an accommodating portion that accommodates the pulling-in member parallel to the outer surface of the outer tube may be provided at the distal end of the inner tube, wherein the holding surfaces may be constituted by the outer surface of the outer tube and a surface of the pulling-in member opposing the outer surface of the outer tube in an accommodated state.

Thus, by moving the inner tube and the outer tube relative to each other in the axial direction, with the inner tube passed through the biological membrane via the hole formed in the biological membrane, the pulling-in member attached to the distal end of the outer tube comes into contact with the inner surface of the biological membrane and is accommodated in the accommodating portion while holding the biological membrane between the outer surface of the outer tube and the surface of the pulling-in member when the outer tube and the pulling-in member are folded and accommodated in the accommodating portion of the inner tube. If the pulling-in member is provided at one location, the biological membrane is pulled in at that one location between the outer surface of the outer tube and the surface of the pulling-in member, and if a plurality of the pulling-in members are provided side-by-side in the circumferential direction of the outer tube, the biological membrane is pulled in at a plurality of locations in the circumferential direction. This allows the access port to be securely fixed in a state in which it penetrates the biological membrane so that it does not come out.

Furthermore, in the above aspect, the outer tube may be provided with two outer tubular portions fitted together so as to be movable relative to each other in the axial direction; strip-shaped pulling-in members formed of a flexible material, one ends of which are attached to distal ends of the individual outer tubular portions, may be individually provided; an accommodating portion that accommodates the individual pulling-in members of the two outer tubular portions in a state in which the pulling-in members are in close contact with each other and parallel to an outer surface of the outer tubular portion at an outer side may be provided at a distal end of the inner tube; and the holding surfaces may be constituted by opposing surfaces of the individual pulling-in members provided on the two outer tubular portions.

Thus, when the inner tube and the outer tube are inserted into the biological membrane through the hole formed in the biological membrane to a position where the pulling-in member disposed at the distal end is disposed inside the biological membrane and the pulling-in member disposed at the rear end is disposed outside the biological membrane, and the two outer tubular portions are moved toward the distal end of the inner tube, with the two outer tubular portions moved relative to each other in the axial direction so that the biological membrane is held between the two pulling-in members, the biological membrane is pulled into the accommodating portion of the inner tube and accommodated therein, while being held between the two pulling-in members. This allows the biological membrane to be accommodated in the accommodating portion, while being held between the two pulling-in members, thus allowing the biological membrane to be pulled in more reliably.

Furthermore, in the above aspect, a surface of the pulling-in member may be provided with a projection.

This can prevent the biological membrane that comes into contact with the pulling-in member from shifting in the surface direction of the pulling-in member owing to the projection, thus making it easy to pull the biological membrane into the accommodating portion.

The present invention provides an advantage in that an access port can be fixed to a biological membrane, such as the pericardium, in a state in which it penetrates the biological membrane.

REFERENCE SIGNS LIST 1 access port
2 inner tube
2e flat surface (opposing surface, holding surface)
3 outer tube
3c flat surface (distal end face, holding surface)
3d outer surface (holding surface)
7, 7b, 7c pulling-in member
7a surface (holding surface)
8 accommodating portion
9 projection
10a, 10b outer tubular portion

The invention claimed is:

1. An access port comprising:
an inner tube and an outer tube fitted together so as to be movable relative to each other in an axial direction,
wherein the inner tube and the outer tube each has holding surfaces having substantially complementary shapes to each other, the holding surfaces are brought close to or away from each other by relative movement of the inner tube and the outer tube,
wherein the holding surfaces comprise a distal end face of the outer tube and an opposing surface provided at a position on a distal end of the inner tube opposing the distal end face,
wherein the diameter of an outer end of the opposing surface is larger than a diameter of an inner end of the distal end face,
wherein the distal end face of the outer tube has a tapered surface shape that tapers toward the distal end, and
the opposing surface of the inner tube has a tapered inner surface shape.

2. The access port according to claim 1, wherein the distal end face and the opposing surface are provided with a protrusion and an indentation, respectively.

3. The access port according to claim 2, wherein the protrusion and the indentation of the distal end face and the opposing surface are provided in a circumferential direction.

* * * * *